US009700721B2

(12) United States Patent
Goodman et al.

(10) Patent No.: US 9,700,721 B2
(45) Date of Patent: Jul. 11, 2017

(54) STIMULATION METHOD FOR TREATMENT OF OCULAR CONDITIONS

(71) Applicant: AUTONOMIC TECHNOLOGIES, INC., Redwood City, CA (US)

(72) Inventors: Amy M. Goodman, San Francisco, CA (US); Anthony V. Caparso, San Francisco, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 7 days.

(21) Appl. No.: 13/917,917

(22) Filed: Jun. 14, 2013

(65) Prior Publication Data
US 2013/0304154 A1 Nov. 14, 2013

Related U.S. Application Data

(63) Continuation-in-part of application No. 13/476,224, filed on May 21, 2012, now Pat. No. 9,456,836, and a continuation-in-part of application No. 13/470,480, filed on May 14, 2012, now Pat. No. 9,220,524.

(60) Provisional application No. 61/659,842, filed on Jun. 14, 2012.

(51) Int. Cl.
*A61N 1/36* (2006.01)
*A61B 17/24* (2006.01)
*A61B 17/34* (2006.01)
*A61N 1/05* (2006.01)
*A61B 17/3211* (2006.01)
*A61B 17/32* (2006.01)

(52) U.S. Cl.
CPC .......... *A61N 1/36046* (2013.01); *A61B 17/24* (2013.01); *A61B 17/3468* (2013.01); *A61N 1/0526* (2013.01); *A61N 1/3606* (2013.01); *A61B 17/3211* (2013.01); *A61B 2017/320052* (2013.01); *A61N 1/0546* (2013.01); *A61N 1/36053* (2013.01); *A61N 1/36153* (2013.01); *A61N 1/36157* (2013.01); *A61N 1/36171* (2013.01); *A61N 1/36175* (2013.01)

(58) Field of Classification Search
CPC ............ A61N 1/36017; A61N 1/36046; A61N 1/3606; A61N 1/36071; A61N 1/0526; A61N 1/36053; A61B 17/00234; A61B 17/3468
USPC ................................ 607/2, 46, 53, 116–118
See application file for complete search history.

(56) References Cited

U.S. PATENT DOCUMENTS

| 7,069,084 B2 * | 6/2006 | Yee ................................. 607/53 |
| 2003/0176898 A1 * | 9/2003 | Gross et al. ..................... 607/54 |
| 2004/0127942 A1 * | 7/2004 | Yomtov ............... A61K 9/0097 607/3 |

(Continued)

*Primary Examiner* — Christopher D Koharski
*Assistant Examiner* — Pamela M Bays
(74) *Attorney, Agent, or Firm* — Tarolli, Sundheim, Covell & Tummino LLP

(57) ABSTRACT

One aspect of the present disclosure relates to a method for modulating, suppressing or preventing an ocular disorder in a subject. One step of the method can include positioning at least one electrode on or proximate to at least one of a sphenopalatine ganglion (SPG), a sphenopalatine nerve (SN), a vidian nerve (VN), a greater petrosal nerve (GPN), a deep petrosal nerve (DPN), or a branch thereof, of the subject. Next, the at least one electrode can be activated to apply an electrical signal to at least one of the SPG, the SN, the VN, the GPN, the DPN, or the branch thereof.

15 Claims, 2 Drawing Sheets

(56) References Cited

U.S. PATENT DOCUMENTS

| | | | |
|---|---|---|---|
| 2004/0220644 A1* | 11/2004 | Shalev et al. | 607/45 |
| 2004/0249416 A1* | 12/2004 | Yun | A61N 1/326 607/2 |
| 2007/0142879 A1* | 6/2007 | Greenberg et al. | 607/62 |
| 2010/0185258 A1* | 7/2010 | Papay | 607/45 |

* cited by examiner

STIMULATION METHOD FOR TREATMENT OF OCULAR CONDITIONS

RELATED APPLICATIONS

The present application is a continuation-in-part of U.S. patent application Ser. No. 13/476,224, filed May 21, 2012, and Ser. No. 13/470,480, filed May 14, 2012, and also claims the benefit of U.S. Provisional Patent Application Ser. No. 61/659,842, filed Jun. 14, 2012. Each of the aforementioned applications is hereby incorporated by reference in its entirety.

TECHNICAL FIELD

The present disclosure relates generally to neuromodulatory methods, and more particularly to methods for treating medical conditions, such as ocular disorders.

BACKGROUND

Most people will have a problem with their eyes at some point in their lives. Most eye problems are not serious and do not require the care of a doctor. For example, certain ocular disorders can cause excessive tearing, chronic swelling or inflammation of eyelids, deficient tear production, or abnormal tear composition. Certain eye diseases, however, are serious and can result in blindness if left untreated.

The tears produced by the human eye are composed of three layers: the outer oily layer; the middle watery layer; and the inner mucus layer. Dry eye syndrome (also known as keratoconjunctivitis, keratitis sicca and xerophthalmia) is often used to describe a condition in which not enough tears are produced, or tears with the improper chemical composition are produced. Symptoms of dry eye syndrome vary in different people, but the following are commonly experienced by those whose tear production is inadequate: irritated, scratchy, dry or uncomfortable eyes; redness of the eyes; a burning sensation of the eyes; a feeling of a foreign body in the eye; blurred vision; excessive watering; and eyes that seem to have lost the normal clear glassy luster. Excessive dry eye can damage eye tissue and possibly scar the cornea, thereby impairing vision.

Blepharitis is a chronic or long-term inflammation of the eyelids and eyelashes. Among the most common causes of blepharitis are poor eyelid hygiene, excess oil produced by the glands in the eyelids, bacterial infection, and allergic reaction. There are two ways in which blepharitis may appear. The most common and least severe, seborrheic blepharitis, is often associated with dandruff of the scalp or skin conditions (e.g., acne). It usually appears as greasy flakes or scales around the base of the eyelashes and as a mild redness of the eyelid. Sometimes, it may result in a roughness of the tissue that lines the inside of the eyelids, or in chalazia, which are nodules on the eyelids. Acute infection of the eyelids can result in styes. Ulcerative blepharitis is a less common, but more severe condition that may be characterized by matted, hard crusts around the eyelashes, which leave small sores that may bleed or ooze when removed. There may also be a loss of eyelashes, distortion of the front edges of the eyelids, and chronic tearing. In severe cases, the cornea may also become inflamed.

Epiphora is the term commonly used to describe a watery eye. More specifically, lacrimation describes persistent welling of tears in the eye, and epiphora is when these tears spill over onto the face. Epiphora is caused by overproduction of tears and/or inadequate/blocked drainage. Both lacrimation and epiphora can be associated with interference in vision, and the surrounding skin can become very sore and excoriated from the constant wiping of tears.

SUMMARY

The present disclosure relates generally to neuromodulatory methods, and more particularly to methods for treating medical conditions, such as ocular disorders.

One aspect of the present disclosure relates to a method for modulating, suppressing or preventing an ocular disorder in a subject. One step of the method can include positioning at least one electrode on or proximate to at least one of a sphenopalatine ganglion (SPG), a sphenopalatine nerve (SN), a vidian nerve (VN), a greater petrosal nerve (GPN), a deep petrosal nerve (DPN), or a branch thereof, of the subject. Next, the at least one electrode can be activated to apply an electrical signal to at least one of the SPG, the SN, the VN, the GPN, the DPN, or the branch thereof.

Another aspect of the present disclosure relates to a method for modulating, suppressing or preventing a tearing disorder in a subject. One step of the method can include positioning at least one electrode on or proximate to at least one of a SPG, a SN, a VN, a GPN, a DPN, or a branch thereof, of the subject. Next, the at least one electrode can be activated to apply an electrical signal to at least one of the SPG, the SN, the VN, the GPN, the DPN, or the branch thereof. The tearing disorder can be selected from the group consisting of epiphora and blepharitis.

Another aspect of the present disclosure relates to a method for modulating, suppressing or preventing a medical condition in a subject. One step of the method can include positioning at least one electrode on or proximate to at least one of a SPG, a SN, a VN, a GPN, a DPN, or a branch thereof, of the subject. Next, the at least one electrode can be activated to apply an electrical signal to at least one of the SPG, the SN, the VN, the GPN, the DPN, or the branch thereof. The medical condition can include dry eye syndrome.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
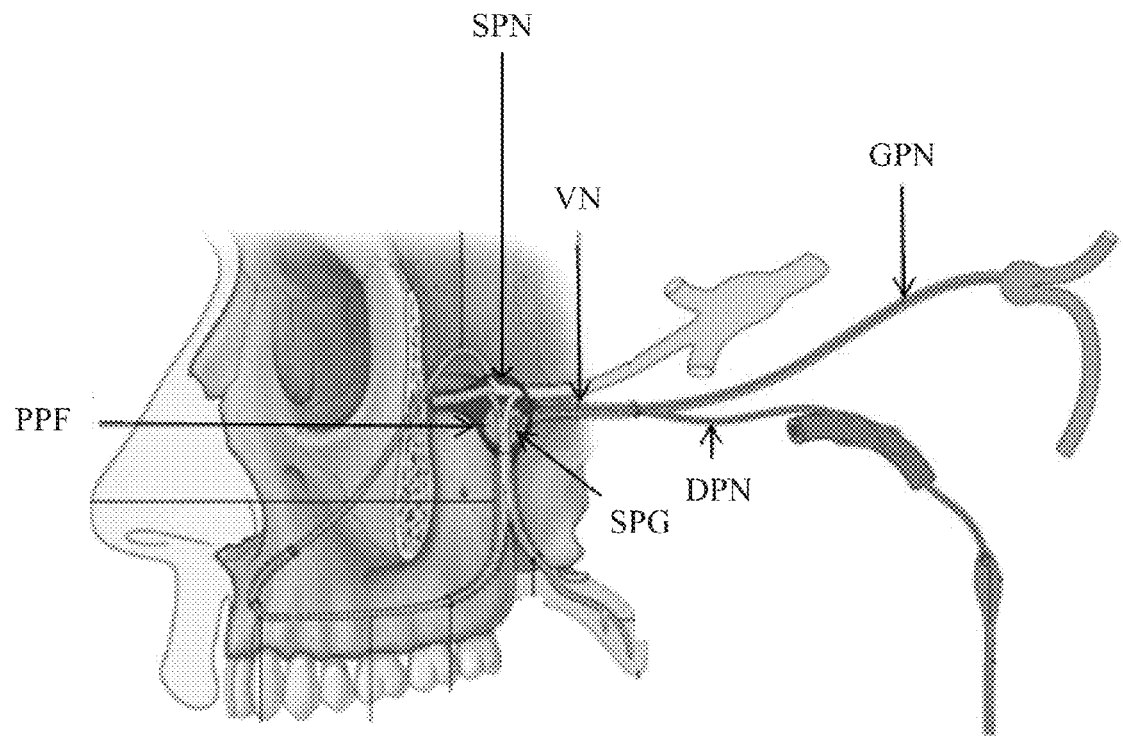
FIG. 1 is a schematic illustration of a lateral view of a human skull showing the position of the infratemporal fossa with the sphenopalatine ganglion lying within the sphenopalatine fossa, as well as the vidian nerve, the deep petrosal nerve, and the greater petrosal nerve.

Unless defined otherwise, all technical and scientific terms used herein have the same meaning as is commonly understood by one of skill in the art to which the present disclosure pertains.

In the context of the present disclosure, the term "in communication" can refer to at least a portion of an electrode being adjacent, in the general vicinity, in close proximity, or directly next to and/or directly on (e.g., in physical contact with) a target nerve or nerve structure, such as a sphenopalatine ganglion (SPG), a sphenopalatine nerve (SPN) (also called the "pterygopalatine nerve"), a vidian nerve (VN) (also called "the nerve of the pterygoid canal"), a greater petrosal nerve (GPN), a lesser petrosal nerve, a deep petrosal nerve (DPN), or a branch thereof (e.g., a nasopalatine nerve, a greater palatine nerve, a lesser palatine nerve, or a superior maxillary nerve). In some instances, the term can mean that at least a portion of an electrode is "in communication" with a target nerve or nerve structure if application of a therapy signal (e.g., an electrical signal) thereto results in a modulation of neuronal activity to elicit a desired response, such as modulation of a nerve signal (e.g., an action potential or electrical impulse) generated in, or transmitted through, the target nerve or nerve structure.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" with reference to activity of a target nerve or nerve structure can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the terms "substantially blocked" or "substantially block" when used with reference to activity of a target nerve or nerve structure can refer to a complete (e.g., 100%) or partial inhibition (e.g., less than 100%, such as about 90%, about 80%, about 70%, about 60%, or less than about 50%) of nerve conduction therethrough. For example, the terms "block", "blocking", and "blockade" can refer to the disruption, modulation, and/or inhibition of nerve impulse transmissions through a target nerve or nerve structure.

As used herein, the term "activity" when used with reference to a target nerve or nerve structure can, in some instances, refer to the ability of a nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on a nerve, neuron, or fiber of a target nerve or nerve structure.

As used herein, the terms "prevent" or "preventing" when used with reference to a medical condition (e.g., an ocular disorder) can refer to stopping a medical condition from occurring, or taking advance measures against the possibility or probability that a medical condition will happen or occur. In some instances, the terms can refer to an action or actions taken to decrease the chance that a subject will contract, develop, or suffer from a medical condition.

As used herein, the terms "suppress" or "suppressing" when used with reference to a medical condition (e.g., an ocular disorder) can refer to refer to any quantitatively or qualitatively measurable or observable reduction or attenuation in a medical condition (e.g., a sign or symptom associated with the medical condition).

As used herein, the term "medical condition mediated by autonomic or neurological dysfunction" can refer to any condition, state, or disease that is characterized, at least in part, by a disruption in nerve signals (e.g., action potentials or electrical impulses) passing through or associated with the autonomic nervous system (ANS). Such medical conditions can result from, be caused by (e.g., directly or indirectly), or otherwise be associated with autonomic or neurological dysfunction. Non-limiting examples of medical conditions mediated by autonomic or neurological dysfunction are provided below.

As used herein, the term "ocular disorder" can refer to any condition, state, or disease of an eye or an associated eye structure (e.g., retina, choroid, lens, cornea, trabecular meshwork, iris, optic nerve, optic nerve head, sclera, anterior or posterior segment, ciliary body, eyelid, conjunctiva, tear duct, or component of the lacrimal drainage system), such as ocular angiogenesis, dry eye, inflammatory conditions, ocular hypertension and ocular diseases associated with elevated intraocular pressure, such as glaucoma.

As used herein, the term "ocular disorder mediated by autonomic or neurological dysfunction" can refer to any condition, state, or disease that is characterized, at least in part, by a disruption in nerve signals (e.g., action potentials or electrical) passing through (or associated with) the ANS that results, either directly or indirectly, in dysfunction or loss of function in an eye or an associated eye structure (e.g., retina, choroid, lens, cornea, trabecular meshwork, iris, optic nerve, optic nerve head, sclera, anterior or posterior segment, ciliary body, eyelid, conjunctiva, tear duct, or component of the lacrimal drainage system).

As used herein, the terms "treat" or "treating" can refer to therapeutically regulating, preventing, improving, alleviating the symptoms of, and/or reducing the effects of a medical condition (e.g., mediated by autonomic or neurological dysfunction). As such, treatment also includes situations where a medical condition, or at least symptoms associated therewith, is completely inhibited, e.g., prevented from happening or stopped (e.g., terminated) such that the subject no longer suffers from the medical condition, or at least the symptom(s) that characterize the medical condition.

Overview

A brief discussion of the pertinent neurophysiology is provided to assist the reader with understanding certain aspects of the present disclosure.

Figure 2:
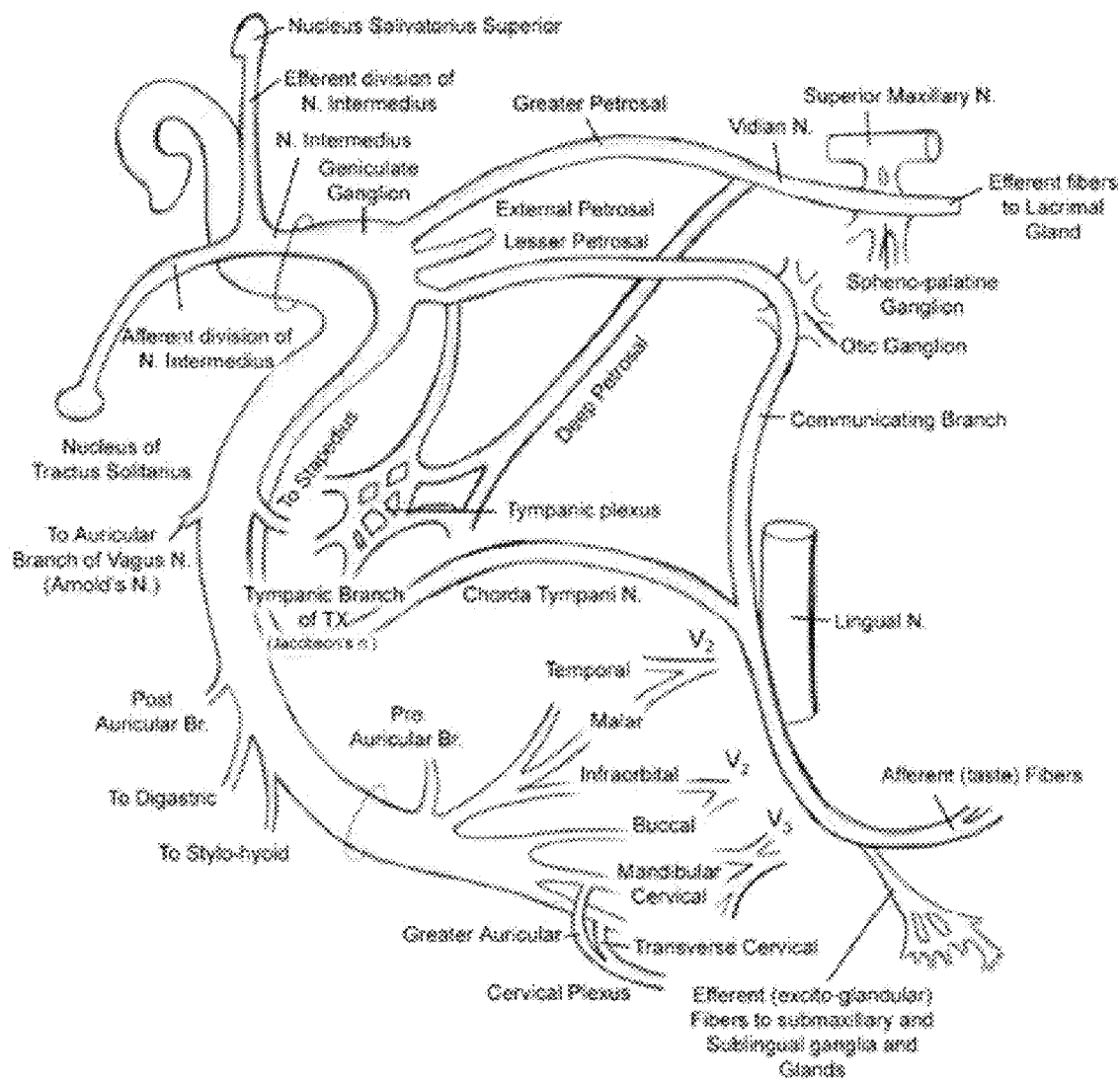
FIG. 2 is a schematic illustration showing the geniculate ganglion and its associated nerve branches.

The SPG (FIGS. 1-2), also called the pterygopalatine ganglion, is located within the pterygopalatine fossa (PPF). The PPF is bounded anteriorly by the maxilla, posteriorly by the medial plate of the pterygoid process and greater wing of the sphenoid process, medially by the palatine bone, and superiorly by the body of the sphenoid process. Its lateral border is the pterygomaxillary fissure, which opens to the infratemporal fossa.

The SPG is a large, extra-cranial parasympathetic ganglion. The SPG is a complex neural ganglion with multiple connections, including autonomic, sensory and motor. The maxillary branch of the trigeminal nerve and the nerve of the pterygoid canal, also known as the VN sends neural projections to the SPG. The fine branches from the maxillary nerve—known as the pterygopalatine nerves or SPN—form the sensory component of the SPG. The SPN pass through the SPG and do not synapse. The GPN (discussed below) carries the preganglionic parasympathetic axons from the superior salivary nucleus to the SPG. These fibers synapse onto the postganglionic neurons within the SPG. The DPN (discussed below) connects the superior cervical sympathetic ganglion to the SPG and carries postganglionic sympathetic axons that again pass through the SPG without any synapses. The DPN and the GPN carry sympathetic and parasympathetic fibers, respectively. The DPN and the GPN carry sympathetic and parasympathetic fibers, respectively. The greater and lesser palatine nerves are branches of the SPG that carry both general sensory and parasympathetic fibers.

The DPN and the GPN join together just before entering the pterygoid canal to form the VN. The DPN is given off from the carotid plexus and runs through the carotid canal lateral to the internal carotid artery. It contains postganglionic sympathetic fibers with cell bodies located in the superior cervical ganglion. It then enters the cartilaginous substance, which fills the foramen lacerum, and joins with the greater superficial petrosal nerve to form the VN. The GPN then passes through the SPG without synapsing, and joins the postganglionic parasympathetic fibers in supplying the lacrimal gland, the nasal mucosa, and the oral mucosa. The GPN is given off from the geniculate ganglion of the facial nerve. It passes through the hiatus of the facial canal, enters the cranial cavity, and runs forward beneath the dura mater in a groove on the anterior surface of the petrous portion of the temporal bone. The GPN enters the cartilaginous substance, which fills the foramen lacerum, and then joins with the DPN to form the VN. The lesser petrosal nerve carries parasympathetic (secretory) fibers from both the tympanic plexus and the nervus intermedius to the parotid gland. The lesser petrosal nerve originates at the geniculate ganglion and passes forwards through its own canal back into the middle cranial fossa.

The VN is housed within the Vidian canal, which is posterior to the SPG. The VN connects to the SPG and contains parasympathetic fibers, which synapse in the SPG, sensory fibers that provide sensation to part of the nasal septum, and also sympathetic fibers. The SPN are sensory nerves that connect the SPG to the maxillary nerve. The SPN traverse through the SPG without synapsing and proceed to provide sensation to the palate. The SPN suspend the SPG in the PPF.

The present disclosure relates generally to neuromodulatory methods, and more particularly to methods for modulating, preventing, suppressing, or treating medical conditions, such as ocular disorders in a subject. Without wishing to be bound by theory, it is believed that abnormal regulation of autonomic pathways, which may be a feature of the medical conditions disclosed herein, can cause excitation, loss of inhibition, suppression, or loss of excitation of these pathways. Thus, in some instances, the present disclosure provides methods for applying one or more therapy signals to a target nerve or nerve structure, such as a SPG, SPN, VN, GPN, DPN and/or a branch thereof (e.g., a nasopalatine nerve, a greater palatine nerve, a lesser palatine nerve, a superior posterior alveolar nerve, or a lesser petrosal nerve) to modulate the transmission of nerve signals and stimulate or block the autonomic pathways passing through the target nerve or nerve structure to modulate, reduce or eliminate one or more symptoms or signs associated with the medical condition. In other instances, it is similarly believed that application of one or more therapy signals to a target nerve or nerve structure (e.g., a SPG, SPN, VN, GPN, DPN and/or a branch thereof) can modulate transmission of nerve signals responsible for provoking or aggravating other undesirable sensations or conditions.

Methods

One aspect of the present disclosure can include a method for modulating, suppressing, preventing, or treating a medical condition, such as an ocular disorder in a subject. Methods of the present disclosure can generally include the steps of: positioning at least one electrode on or proximate to a target nerve or nerve structure (e.g., a SPG, SPN, VN, GPN, DPN and/or a branch thereof) of the subject; and activating the at least one electrode to apply a therapy signal (e.g., an electrical signal) to the target nerve or nerve structure. In some instances, the methods of the present disclosure can act to suppress or prevent the medical condition by disrupting nerve signals passing through the ANS as the signals traverse, or are generated in, the target nerve or nerve structure. To treat a medical condition mediated by dysfunction of the parasympathetic nervous system, for example, the GPN and/or a branch thereof may be modulated according to the present disclosure. Alternatively, to treat a medical condition mediated by dysfunction of the sympathetic nervous system, the DPN and/or a branch thereof may be modulated according to the present disclosure.

In some instances, medical conditions that can be modulated, suppressed, prevented, or treated by the present disclosure can include ocular disorders (e.g., mediated by autonomic or neurological dysfunction). Without wishing to be bound by theory, it is believed that the abnormal regulation of sensory pathways can cause abnormal nerve signal transmission through autonomic pathways innervating the eye and/or structures associated with the eye. Thus, applying one or more therapy signals (e.g., an electrical signal) to a target nerve or nerve structure (e.g., a SPG, SPN, VN, GPN, DPN and/or a branch thereof) can modulate (e.g., substantially block) the transmission of aberrant nerve signals and stimulate feedback of the pathways passing therethrough to reduce or eliminate symptoms associated with the ocular disorder.

In one example, ocular disorders (e.g., mediated or caused by autonomic or neurological dysfunction) that can be suppressed, prevented, or treated by the present disclosure can include tearing disorders, such as epiphora and blepharitis.

In another example, an ocular disorder (e.g., mediated or caused by autonomic or neurological dysfunction) that can be suppressed, prevented, or treated by the present disclosure can include dry eye syndrome.

In another aspect, the at least one electrode can include any mono-polar, bipolar, or mutli-polar electrode configured to deliver an electrical signal to a target nerve or nerve structure (e.g., a SPG, SPN, VN, GPN, DPN and/or a branch thereof). In some instances, the at least one electrode can be securely disposed on or within a housing or casing (e.g., made of silicon, metal or plastic). In other instances, the at least one electrode can be securely disposed on a percutaneous lead. Alternatively, the electrode can be configured as a cuff-type electrode. In further instances, the at least one electrode can comprise one component of a neurostimulator. In such instances, the neurostimulator can comprise any active implantable medical device configured to deliver electrical stimulation, alone or in combination with other types of stimulation, to a target nerve or nerve structure (e.g., a SPG, SPN, VN, GPN, DPN and/or a branch thereof) of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the subject's tissue (e.g., therapeutic agent delivery mechanisms, sensors, etc.). The neurostimulator can further include, or at least be in electrical communication with, a power source that provides the energy source for electrical stimulation.

One or a combination of surgical methods may be used to implant the at least one electrode on or adjacent to a target nerve or nerve structure (e.g., a SPG, SPN, VN, GPN, DPN and/or a branch thereof) such that the at least one electrode is in electrical communication with the target nerve or nerve structure. In some instances, a percutaneous technique can be used to implant the at least one electrode. Examples of percutaneous techniques that may be employed are disclosed in U.S. Pat. No. 6,526,318 (hereinafter, "the '318 patent"), as well as U.S. patent application Ser. Nos. 13/476,224 (hereinafter, "the '224 application") and 13/470,480 (hereinafter, "the '480 application"). Because the SPG, VN, and SPN are in very close proximity to one another within a very small area, the same technique can be applied to achieve placement of at least one electrode on or adjacent to any of the three structures. It should also be understood that, because the region in which the target nerves or nerve structures of the present disclosure all join together is very small, stimulation of a target nerve or nerve structure, even when an electrode is placed optimally, may also stimulate two or all of the other structures.

It will also be understood that surgical methods other than percutaneous approaches may be used to implant an electrode on or proximate to a target nerve or nerve structure. In one example, at least one electrode can be positioned on the skin of a subject adjacent (e.g., directly adjacent) a target nerve or nerve structure (e.g., a SPG, SPN, VN, GPN, DPN and/or a branch thereof) so that an electrical signal can be transcutaneously delivered to the target nerve or nerve structure. In another example, an intravascular approach can be used so that at least one electrode is positioned adjacent (e.g., directly adjacent) a target nerve or nerve structure. An electrical signal can then be delivered to the electrode so that electrical energy is transvascularly delivered to the target nerve or nerve structure.

In some instances, the at least one electrode can be implanted in the subject without penetrating the cranium of the subject.

In other instance, the at least one electrode can be implanted in the subject without penetrating the nasal cavity and/or the palate of the subject.

In another aspect, a therapy signal can be applied to the target nerve or nerve structure (e.g., a SPG, SPN, VN, GPN, DPN and/or a branch thereof) to modulate activity associated with the target nerve or nerve structure and thereby prevent or suppress the medical condition (e.g., the ocular disorder). Neuromodulation of the SPG, for example, can be done directly or indirectly by affecting postganglionic neurons located within the SPG and/or their corresponding axons, or the preganglionic axons in the VN that synapse with the SPG, respectively. Examples of therapy signals that may be applied to a target nerve or nerve structure can include electrical energy, chemical agents, mechanical force, thermal energy, and combinations thereof.

In some instances, the therapy signal can be an electrical signal. Electrical stimulation may be delivered in any of several forms, such as biphasic charge-balanced pulses having a frequency of about 1-1000 Hz (e.g., 5-200 Hz), a pulse-width of about 0.04-2 ms, a current of about 0.05-100 mA (e.g., 0.1-5 mA), and a voltage of about 1-10 V. In addition, electrical modulation can be controllable such that either anodic or cathodic stimulation may be applied. Stimulation may be delivered continuously, intermittently, as a burst in response to a control signal, or as a burst in response to a sensed parameters, such as increased SPG neural activity. The electrical parameters may also be adjusted automatically based on a control signal, based on sensed parameters, or by selection by the subject.

In some instances, electrical energy can be applied to a target nerve or nerve structure (e.g., a SPG 100, SPN 103, VN 102, GPN, DPN and/or a branch thereof) for a time and in an amount insufficient to cause a lesion on the target nerve or nerve structure.

In another aspect, an electrode may be utilized which, instead of or in addition to delivering electrical stimulation to the target nerve or nerve structure, delivers a medication solution or analgesic to the target nerve or nerve structure. For example, an electrode may be used that has a small port at its tip, which is connected to a reservoir or medication pump containing a medication solution or an analgesic (e.g., an anesthetic solution). The medication/analgesic delivery electrode may be implanted using the same procedure as used for the electrical stimulation electrode. If desired by the subject or physician, the reservoir or medication pump may also be implanted in the subject's body (e.g., similar or identical to an implantable pulse generator). In some instances, the electrode can be controllable such that the amount of medication solution or analgesic applied, the rate at which medication solution or analgesic is applied, and the time period over which the medication solution or analgesic is applied is adjustable.

It should be understood that delivery of a medication solution or analgesic from an electrode (or a structure associated with an electrode) may be used alone or in conjunction with the electrical stimulation method described above. For example, a device (e.g., a conduit having one or more electrodes disposed thereon) may be used that is capable of either producing an electrical signal or delivering a medication solution or analgesic. As another example, an electrostimulatory approach could be applied to a target nerve or nerve structure (e.g., a SPG, SPN, VN, GPN, DPN and/or a branch thereof) of one side of a subject's face, while the method utilizing delivery of a medication solution or analgesic could be applied to the same or different target nerve or nerve structure on the other side of the subject's face.

Advantageously, once the at least one electrode is placed into communication with the target nerve or nerve structure, application of one or more therapy signals (e.g., electrical signals) can be adjusted to the subject's individual needs (e.g., by the subject or via a closed-loop system) without requiring further surgical intervention.

In one example of the present disclosure, a neurostimulator (not shown) can be implanted in or about the PPF to deliver an electrical signal to a SPG, SPN, VN and/or a branch thereof. The neurostimulator can be configured identically or similarly as the neurostimulator disclosed in the '224 application. For instance, the neurostimulator can include a pulse generator, an integral lead system, and an integral fixation plate. The neurostimulator can be delivered to the PPF in an identical or similar fashion as disclosed in the '480 application. Briefly, for example, a gingival-buccal surgical approach can be used whereby a trans-oral incision is first created. An introducer (not shown) is then inserted into the incision and advanced posteriorly, superiorly and medially toward the PPF. The introducer is carefully advanced so as to maintain contact with the posterior maxilla.

Once a distal end of the introducer is placed within the PPF, the neurostimulator can be advanced within a pre-defined groove of the introducer into the PPF. The neurostimulator is surgically placed such that the integral lead (with at least one stimulation electrode (not shown)) located within the PPF directly on or adjacent to the SPG, SPN, VN and/or a branch thereof. The integral fixation plate of the neurostimulator is securely anchored to the zygomatic process of the maxilla. Following fixation of the neurostimulator, the neurostimulator can be activated so that the stimulation electrode delivers an electrical signal to the SPG, SPN, VN and/or a branch thereof to modulate (e.g., substantially block) nerve signal transmission therethrough.

In another example of the present disclosure, an intravascular approach may be used to deliver one or more electrical signals to the DPN and/or a branch thereof. In some instances, an appropriately-sized intravascular device, such as one identically or similarly configured as the devices disclosed in U.S. patent application Ser. No. 11/641,331 may be used. In such instances, the intravascular device may be advanced through the vasculature (e.g., an artery or vein) of a subject to a location adjacent (e.g., directly adjacent) or proximate to the DPN and/or a branch thereof such that delivery of an electrical signal to the intravascular device is effective to modulate autonomic activity associated therewith (e.g., modulating sympathetic activity). In one example, an intravascular device can be positioned at a location in the internal carotid artery adjacent (e.g., directly adjacent) or proximate to the DPN and/or a branch thereof such that delivery of an electrical signal to the intravascular device is effective to modulate sympathetic activity in the subject. In another example, an intravascular device can be positioned at a location in the internal jugular vein adjacent (e.g., directly adjacent) or proximate to the DPN and/or a branch thereof such that delivery of an electrical signal to the intravascular device is effective to modulate sympathetic activity in the subject. It will be appreciated that electrical signals can be delivered to the intravascular device either directly (e.g., via a lead) or wirelessly. Alternatively, the intravascular device may be self-powered by, for example, a battery that may be remotely or inductively charged as needed.

In another example of the present disclosure, one or a combination of percutaneous techniques may be used to target the GPN and/or a branch thereof such that delivery of an electrical signal to the at least one electrode is effective to modulate autonomic activity associated therewith (e.g., parasympathetic activity). In one approach, an electrode may be placed on or proximate to the GPN and/or a branch thereof via the paryngotympanic tube, which may be accessed via the nasopharynx of a subject. In another approach, at least one electrode may be placed on or proximate to the GPN and/or a branch thereof via the backside of the inner ear. Alternatively, an electrode may be placed on a portion of the wall of Meckel's cave, which may be accessed via the foramen ovale such that delivery of an electrical signal to the at least one electrode is effective to modulate parasympathetic activity in the subject.

From the above description of the present disclosure, those skilled in the art will perceive improvements, changes and modifications. For example, it will be appreciated that the methods of the present disclosure can be performed to apply modulate activity of a target nerve or nerve structure (e.g., a SPG, SPN, VN, GPN, DPN and/or a branch thereof) on either or both sides of a subject's head. Such improvements, changes, and modifications are within the skill of those in the art and are intended to be covered by the appended claims. All patents, patent applications, and publication cited herein are incorporated by reference in their entirety.

The following is claimed:

1. A method for modulating, suppressing or preventing an ocular disorder in a subject, the method comprising the steps of:
   receiving at least one electrode on or proximate to at least one of a sphenopalatine ganglion (SPG), a sphenopalatine nerve (SN), a vidian nerve (VN), a greater petrosal nerve (GPN), a deep petrosal nerve (DPN), or a branch thereof, of the subject; and
   activating the at least one electrode, wherein the at least one electrode is configured to apply an electrical signal to at least one of the SPG, the SN, the VN, the GPN, the DPN, or the branch thereof to modulate, suppress or prevent the ocular disorder, the electrical signal having a frequency of about 1 to 1000 Hz, a pulse-width of about 0.04 to 2 ms, a current of about 0.05 to 100 mA, and a voltage of about 1 to 10 V; wherein the ocular disorder is mediated by autonomic or neurological dysfunction.

2. The method of claim 1, wherein the electrical signal disrupts nerve signal generation in, or transmission through, at least one of the SPG, the SN, the VN, the GPN, the DPN, or the branch thereof.

3. The method of claim 1, wherein the at least one electrode is received without penetrating the cranium, into the pterygopalatine fossa so that the at least one electrode is positioned on or proximate to at least one of the SPG, the SN, the VN, or the branch thereof.

4. The method of claim 1, wherein the activating step generates heat insufficient to cause a lesion on at least one of the SPG, the SN, the VN, the GPN, the DPN, or the branch thereof.

5. The method of claim 1, further including the step of adjusting the electrical signal without requiring an invasive procedure on the subject.

6. The method of claim 1, wherein the at least one electrode is received proximate to the GPN, the DPN, or a branch thereof, via an intravascular route.

7. A method for modulating, suppressing or preventing a tearing disorder in a subject, the method comprising the steps of:
   receiving at least one electrode on or proximate to at least one of a SPG, a SN, a VN, a GPN, a DPN, or a branch thereof, of the subject; and
   activating the at least one electrode wherein the at least one electrode is configured to apply an electrical signal to at least one of the SPG, the SN, the VN, the GPN, the DPN, or the branch thereof to modulate, suppress or prevent the tearing disorder, the electrical signal having a frequency of about 1 to 1000 Hz, a pulse-width of about 0.04 to 2 ms, a current of about 0.05 to 100 mA, and a voltage of about 1 to 10 V; wherein the tearing disorder is mediated by autonomic or neurological dysfunction.

8. The method of claim 7, wherein the at least one electrode is received without penetrating the cranium, into the pterygopalatine fossa so that the at least one electrode is positioned on or proximate to at least one of the SPG, the SN, the VN, or the branch thereof.

9. The method of claim 7, wherein the activating step generates heat insufficient to cause a lesion on at least one of the SPG, the SN, the VN, the GPN, the DPN, or the branch thereof.

10. The method of claim 7, further including the step of adjusting the electrical signal without requiring an invasive procedure on the subject.

11. The method of claim 7, wherein the at least one electrode is received proximate to the GPN, the DPN, or a branch thereof, via an intravascular route.

12. A method for modulating, suppressing or preventing a dry eye syndrome in a subject, the method comprising the steps of:
receiving at least one electrode on or proximate to at least one of a SPG, a SN, a VN, a GPN, a DPN, or a branch thereof, of the subject; and
activating the at least one electrode, wherein the at least one electrode is configured to apply an electrical signal to at least one of the SPG, the SN, the VN, the GPN, the DPN, or the branch thereof to modulate, suppress, or prevent the dry eye syndrome, the electrical signal having a frequency of about 1 to 1000 Hz, a pulse-width of about 0.04 to 2 ms, a current of about 0.05 to 100 mA, and a voltage of about 1 to 10 V; wherein the dry eye syndrome is mediated by autonomic or neurological dysfunction.

13. The method of claim 12, wherein the electrical signal disrupts nerve signal generation in, or transmission through, at least one of the SPG, the SN, the VN, the GPN, the DPN, or the branch thereof.

14. The method of claim 12, wherein the at least one electrode is received without penetrating the cranium, into the pterygopalatine fossa so that the at least one electrode is positioned on or proximate to at least one of the SPG, the SN, the VN, or the branch thereof.

15. The method of claim 12, wherein the at least one electrode is received proximate to the GPN, the DPN, or a branch thereof, via an intravascular route.

* * * * *